United States Patent [19]
Forkey et al.

[11] Patent Number: 5,688,224
[45] Date of Patent: Nov. 18, 1997

[54] MEDICAL VISUALIZATION DEVICE

[75] Inventors: Richard E. Forkey, Westminster; David M. Tremblay, Charlton; Christopher B. Smith, Gardner, all of Mass.

[73] Assignee: Precision Optics Corporation, Gardner, Mass.

[21] Appl. No.: 541,200

[22] Filed: Oct. 16, 1995

[51] Int. Cl.$^6$ .................................................. A61B 1/26
[52] U.S. Cl. ........................... 600/200; 600/129; 600/245; 600/246
[58] Field of Search .................... 600/127, 129, 600/200; 604/38, 78, 173

[56] References Cited

U.S. PATENT DOCUMENTS

| | | |
|---|---|---|
| 3,020,912 | 2/1962 | Chester . |
| 3,224,437 | 12/1965 | Hardgrove .................. 600/200 |
| 3,373,737 | 3/1968 | Moore et al. . |
| 3,384,076 | 5/1968 | Speelman . |
| 3,664,330 | 5/1972 | Deutsch ...................... 600/246 |
| 3,728,998 | 4/1973 | Heine . |
| 3,978,850 | 9/1976 | Moore et al. . |
| 4,380,998 | 4/1983 | Kieffer et al. . |
| 4,567,881 | 2/1986 | Heller . |
| 4,622,967 | 11/1986 | Schachar . |
| 4,685,452 | 8/1987 | Riester . |
| 4,766,886 | 8/1988 | Juhn . |
| 4,785,796 | 11/1988 | Mattson ...................... 600/200 |
| 4,913,132 | 4/1990 | Gabriel . |
| 5,038,755 | 8/1991 | Burgio et al. . |
| 5,345,926 | 9/1994 | Chikama . |

FOREIGN PATENT DOCUMENTS

| | | |
|---|---|---|
| 203784 | 9/1923 | United Kingdom . |
| 494280 | 10/1938 | United Kingdom . |
| 2 071 503 | 9/1981 | United Kingdom . |
| 2 090 531 | 7/1982 | United Kingdom . |
| 2 105 994 | 4/1983 | United Kingdom . |
| 2 185 688 | 7/1987 | United Kingdom ............ A61B 1/22 |

Primary Examiner—Beverly M. Flanagan
Attorney, Agent, or Firm—Pearson & Pearson

[57] ABSTRACT

A medical visualization device for examination of an anatomical area through a body orifice for diagnosis or local therapeutic treatment. The device comprises a fiber optic handle and a distal tip which incorporates a viewing lens. The distal tip further comprises access means for insertion of hypodermic needle to perform an injection of therapeutic substances.

16 Claims, 2 Drawing Sheets

MEDICAL VISUALIZATION DEVICE

BACKGROUND OF THE INVENTION

The invention relates to optical medical instruments and in particular to a medical visualization device for medical examination by visualizing of an anatomical area through a body orifice with the ability to perform local therapeutic treatment.

Viewing scopes that enable one to view body passages are well known in the art. For medical applications the viewing scopes take many forms and are known by different names. Generically the name "endoscope" means any slender, tubular optical instrument used as a viewing system for examining an inner body part. In particular, such viewing scopes have a variety of names, such as endoscopes, laparoscopes and bronchoscope.

Various medical instruments have been used to examine an anatomical area through a body orifice such as ear, nose, mouth, vagina, urethra, rectum, etc. However, these instruments have not provided access for hypodermic or other therapeutic substance application directly through the viewing chamber.

A well known device is called a sigmoidoscope used in rectal examinations having optical means to aid visualization, but this device uses lenses at both distal and proximal extremities or no lenses at all. Other similar devices are configured for gynecological and otolaryngological examination.

SUMMARY

It is an object of this invention to provide a medical visualization device for examination of an anatomical area through a body orifice for diagnosis or local therapeutic treatment.

It is another object of this invention to provide a medical visualization device having viewing magnification for examination of an anatomical area through a body orifice.

It is still another object of this invention to provide a medical visualization device which provides the means for application of medication through a distal tip of the device.

It is a further object of this invention to provide a medical visualization device having a low-cost disposable distal tip.

The objects are further accomplished by a medical visualization device comprising a handle means for providing illumination and facilitating use of the visualization device, a distal tip means attached to the handle means for insertion into an orifice, the distal tip means comprises a lens means, arranged at a proximal end of the distal tip means, for viewing an illuminated area at a distal end. The handle means provides the illumination by transferring light entering the handle at a first portion to a second portion of the handle, the light being emitted adjacent to the lens means. A light source provides light to the first portion of the handle. The lens means provides magnification of the illuminated viewing area. The distal tip means comprises an access port means for enabling insertion of a needle means for providing therapeutic treatment. The handle means comprises a fiber optic cable for transferring light to the lens means. The light exits the fiber optic cable in the direction of the lens means at an angle conforming with the slope of the lens means.

The objects are further accomplished by a medical visualization device comprising a handle means for providing illumination and facilitating use of the visualization device, a distal tip means attached to the handle means for insertion into an orifice, the distal tip means comprises an access port means for enabling insertion of a needle means for providing therapeutic treatment. The handle means provides the illumination by transferring light entering the handle at a first portion to a second portion of the handle, the light being emitted adjacent to the lens means. The light source provides light to the first portion of the handle. The handle means comprises a fiber-optic cable for transferring light to the lens means. The light exits the fiber optic cable in the direction of the lens means at an angle conforming with the slope of the lens means.

The objects are further accomplished by a medical visualization device comprising a handle having a fiber optic cable light output at a first end and light guide fitting for connecting to a light source on a second end of the cable, a distal tip attached to the handle, the distal tip comprises a lens at a proximal end positioned adjacent to the fiber optic cable light output of the handle, the lens provides magnification of a viewing area at the distal end of the distal tip, and the distal tip comprises at least one access port for enabling an insertion of a needle into the distal tip and guidance to the viewing area. The distal tip is secured to the handle by means of a set screw inserted into the handle enabling the distal tip to be easily removed from the handle after use.

The objects are further accomplished by a method for providing therapeutic treatment with a medical visualization device inserted into a body orifice comprising the steps of providing illumination through a handle with a fiber optic cable, attaching a distal tip to the handle, the distal tip comprises a lens positioned adjacent to the illumination from the handle, and inserting a needle in the distal tip for providing the therapeutic treatment to a lighted area at the end of the distal tip. The method further comprises the steps of providing a light source to the fiber optic cable and securing the distal tip to the handle with a set screw inserted into the handle to enable the distal tip to be easily removed after use.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF THE PREFERRED EMBODIMENT

Figure 1:
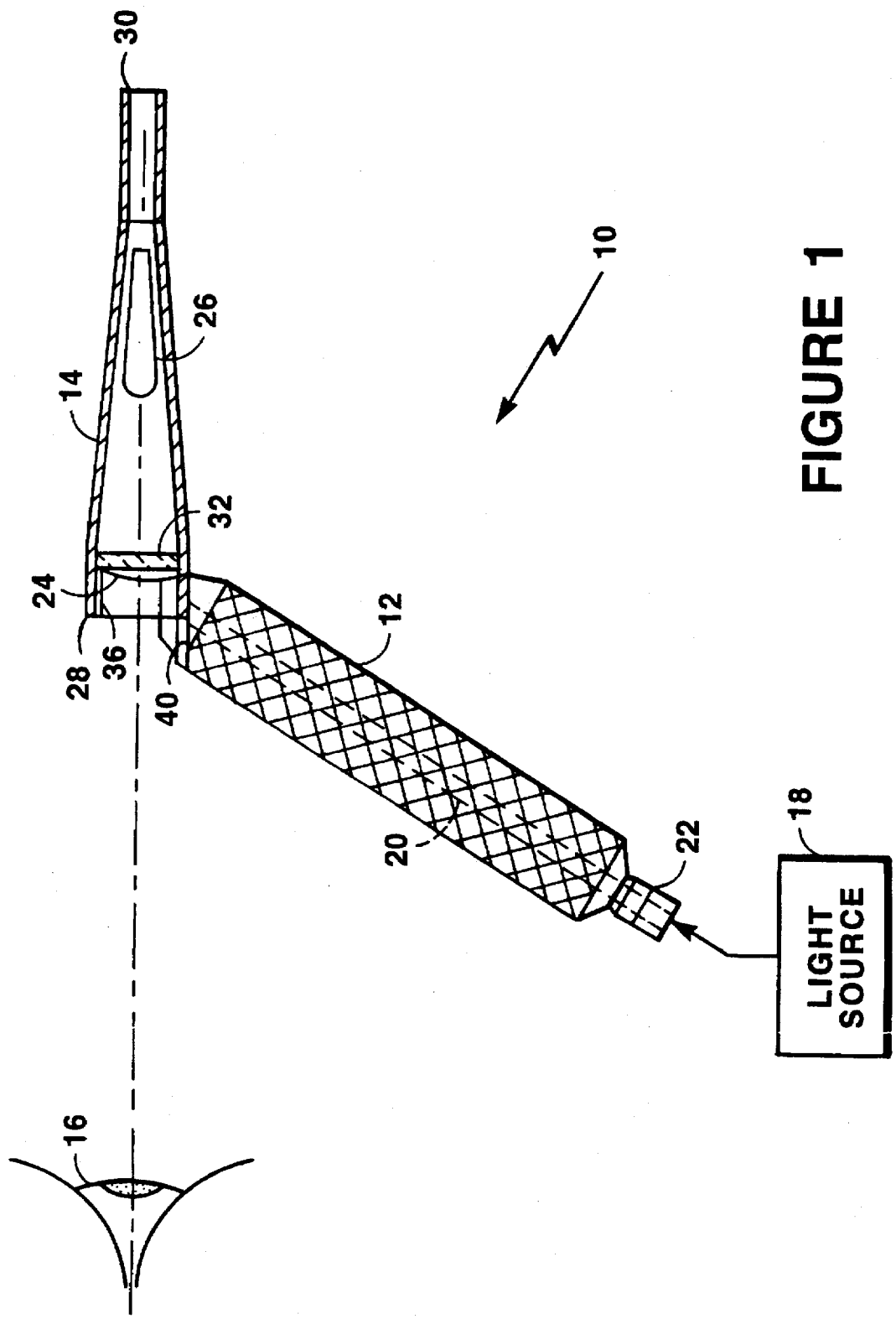
FIG. 1 is a view of the invention, partially in section, of a medical visualization device showing a handle and a cross-section of a distal tip portion of the device attached to the handle.
Figure 2:
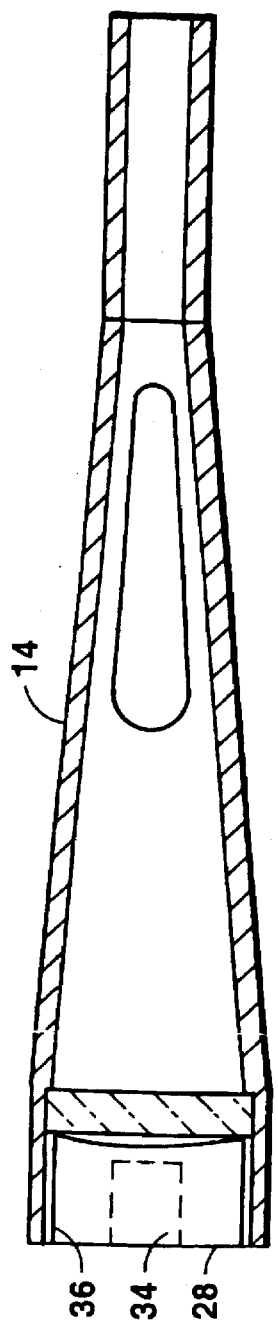
FIG. 2 is a cross-section of a distal tip along a plane showing a slot in a proximal end for attaching the distal tip to a handle.

Referring to FIG. 1 and FIG. 2, a medical visualization device 10 is shown comprising a handle 12 and a distal tip 14. The handle 12 provides for connection to a light source 18 and for transfer of light through the handle 12 via a fiber optic cable 20 passing through the center of the handle 12. The fiber optic cable 20 transfers light to the distal tip 14.

The handle 12 is attached to the distal tip 14 by means of a slot 34 in the proximal end 28 of the distal tip 14, as shown in FIG. 2, fitting into grooves 40 near the top of the handle 12. A set screw is inserted into a threaded hole (not shown) approximately one-half inch from the top of the handle 12 at a 20 degree angle from the outer surface of the handle 12. When the set screw is tightened it engages the outer wall of the distal tip 14.

The length of the handle 12 including a light source guide fitting 22 is approximately 4.723 inches. The handle 24 is made of aluminum having a knurled surface for a positive grip when in use. The aluminum may be embodied by Type 2024 manufactured by Admiral Metals, of Woburn, Mass., U.S.A. The fiber optic cable may be embodied by type N.A. 0.66–0.68, size 0.0015 inches, core 89%, and clad 11%, manufactured by Electro Fiber Optics, of Marlborough, Mass., U.S.A.

The distal tip 14 body is made from delrin which may be obtained from AIN Plastics of Norwood, Mass., U.S.A. The distal tip 14 is typically 4 inches in length. It has an outside diameter at the proximal end 28 of 0.8 inches and at the distal extremity 30 the outside diameter is typically 0.341 inches. The lens 24 is placed into an opening provided in a lens mounting support holder 32 and a cylindrical retainer 36 is positioned against the perimeter of the lens 24 and glued in place.

The distal tip 14 comprises a viewing lens 24 with an anti-reflection coating and may be a single or multiple-element lens arranged at the proximal end 28 of the distal tip 14. FIG. 1 shows a single viewing lens 24 having a 110 mm focal distance and an outside maximum diameter of 0.689 inches. The lens 24 in the present embodiment has a 2.5× magnification. However, magnifications ranging from 2× to 50× may be employed in other embodiments contemplated. The lens may be embodied by glass type BK-7, manufactured by Schott, of Duryea, Pa., U.S.A. The lens 24 has a radius first surface of 56.85 mm, a radius second surface plano, and a center thickness of 4.0 mm. The lens coating comprises a conventional single-layer MgFl for visual wavelength and may be embodied by type AR-100, manufactured by Precision Optics Corporation, of Gardner, Mass., U.S.A.

Figure 3:
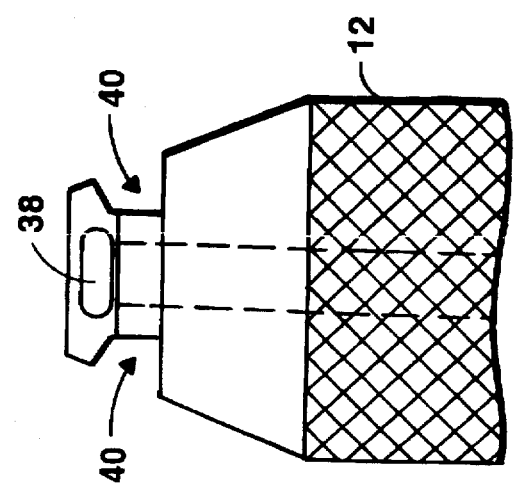
FIG. 3 is a front view of handle showing an opening near the top of the handle for positioning the light output end of a fiber optic cable running through the handle.

Referring to FIG. 1 and FIG. 3, the viewing lens 24 is configured so that the eye 16 of a visual observer may see the region at or near distal extremity 30 of the distal tip 14 even by locating the observer's eye 16 a fair distance (such as 1" to 10" typical) behind the proximal lens 24. The fiber optic cable 20 terminates at an opening 38 at the top of the handle 12, as shown in FIG. 3, which is positioned adjacent to the lens 24, and light is emitted from the polished end of the fiber optic cable 20 at an angle conforming with the slope of the lens 24 resulting in negligible backscatter.

The distal tip 14 includes an access means 26, such as one or more openings in the wall of the distal tip 14, to allow the insertion of hypodermic needles to perform injections. One access means 26 is shown in the cross-section view in the FIG. 1, but in the preferred embodiment there are three access means 26 spaced 120 degrees around the perimeter of the distal tip 14. The access means 26 allows a straight needle to be inserted into the distal tip 26 and guided to the distal extremity 30 to accomplish therapeutic treatment. The insertion of the needle into the distal tip 14 access means 26 may be observed in reasonable focus so that the medical visualization device 10 may be used as an aid to the application of a therapeutic substance.

The medical visualization device 10 provides for visualizing an anatomical area through a body orifice such as ear, nose, mouth, vagina, urethra, rectum, etc. in order to perform medical examination for diagnosis or enables local therapeutic treatment by application of therapeutic drugs or other agents to local parts of the body. A person of ordinary skill in the art will recognize that the medical visualization device 10 may, with proper lens assembly and mechanical interface at the proximal end 28 of the distal tip 14, be used to allow visualization by electronic means such as video camera, telemedicine sensor and the like which then electronically provides an image to an observer, such as viewing on a video monitor. Further, another embodiment of the distal tip 14 may be employed without a lens 24 in the proximal end 28.

One important application of the medical visualization device 10 is for diagnosis examination and local therapeutic treatment for female incontinence. As noted above, the length of the distal tip 14 is typically 4 inches and the diameter of the proximal end 28 is 0.8 inches. The distal tip 14 is sized at an outside diameter of the distal extremity 30 of no greater than standard medical catheter sizing of "26 French" (0.341 inches or 8.7 mm) to allow insertion into the urethra to allow the distal extremity 30 (25 mm or less from the proximal opening of the urethra) to be in contact or close proximity to the urethral sphincter, controlling urine flow from the bladder. Side access means 26 or ports in the distal tip 14 allow access to the sphincter for injection of "bulking agents" (such as collagen compounds, vulcanized silicone, etc.) to fill out the slackened sphincter muscles. This device 10 provides about 2.5× magnification, and a doctor may view the sphincter with his eye very close or 8 to 10 inches or more distant from the Medical Visualization Device 10. This embodiment may incorporate a reasonable cost, disposable distal tip 14 and a re-usable, sterilizable (even by autoclave), fiber optic handle 12. The fact that the end of the fiber optic cable 20 of handle 12 is located behind the lens 24 of the distal tip 14 and outside any apparent requirement for a "sterile field", may not require sterilization of the handle 12. Further, this embodiment enables the doctor, being shielded from the bladder and sphincter, to complete diagnostic and therapeutic operations with minimum interference from urine discharge.

This invention has been disclosed in terms of a certain embodiment. It will be apparent that many modifications can be made to the disclosed apparatus without departing from the invention. For example, the distal tip 14 may be embodied without a lens 24 thereby providing for direct view of an anatomical area of a body. Further, another embodiment of this device 10 accepts curved needles whereas the present embodiment is for straight needles. Therefore, it is the intent of the appended claims to cover all such variations and modifications as come within the true spirit and scope of this invention.

We claim:

1. A medical visualization device comprising:
    handle means for facilitating use of said visualization device, said handle means comprises means for transferring light through said handle means;
    distal tip means attached to said handle means for insertion into an orifice, said distal tip means comprises a lens means, arranged at a proximal end of said distal tip means, for viewing an area at a distal end of said tip means illuminated by said light from said handle means; and
    said distal tip means comprises an access port means in a wall of said distal tip means located a predetermined distance from said distal end for enabling insertion of a needle means for providing therapeutic treatment.

2. The medical visualization device as recited in claim 1 wherein said means for transferring light comprises a fiber optic cable extending from a first portion to a second portion of said handle means, said light being emitted adjacent to said lens means.

3. The medical visualization device as recited in claim 2 wherein a light source provides light to said first portion of said handle means.

4. The medical visualization device as recited in claim 1 wherein said lens means provides magnification of said illuminated viewing area.

5. The medical visualization device as recited in claim 1 wherein said handle means comprises a knurled surface for providing a positive grip when being used.

6. The medical visualization device as recited in claim 2 wherein said fiber optic cable emits light in the direction of said lens means at an angle conforming with a predetermined slope of said lens means.

7. A medical visualization device comprising:
   handle means for facilitating use of said visualization device, said handle means comprises means for transferring light from a first portion to a second portion;
   distal tip means having a proximal end attached to said handle means for insertion into an orifice, said light from said second portion of said handle means passes through said distal tip means illuminating an area adjacent to a distal end of said distal tip means; and
   said distal tip means comprises an access port means in a wall of said distal tip means located a predetermined distance from said distal end for enabling insertion of a needle means for providing therapeutic treatment.

8. The medical visualization device as recited in claim 7 wherein said means for transferring light comprises a fiber optic cable extending from said first portion to said second portion of said handle means.

9. The medical visualization device as recited in claim 8 wherein a light source provides light to said first portion of said handle means.

10. The medical visualization device as recited in claim 7 wherein said handle means comprises a knurled surface for providing a positive grip when being used.

11. The medical visualization device as recited in claim 8 wherein said fiber optic cable emits light in the direction of said distal end of said distal tip means.

12. A medical visualization device comprising:
   a handle having a fiber optic cable light output at a first end and light guide fitting means for connecting to a light source on a second end of said cable;
   a distal tip attached to said handle, said distal tip comprises a lens at a proximal end positioned adjacent to said fiber optic cable light output of said handle;
   said lens provides magnification of a viewing area at the distal end of said distal tip; and
   said distal tip comprises at least one access port in a wall of said distal tip located a predetermined distance from said distal end for enabling an insertion of a needle into said distal tip and guidance to said viewing area.

13. The medical visualization device as recited in claim 12 wherein:
   said distal tip is secured to said handle by means of a set screw inserted into the handle enabling said distal tip to be easily removed from said handle after use.

14. A method for providing therapeutic treatment with a medical visualization device inserted into a body orifice comprising the steps of:
   providing illumination through a handle of said medical visualization device having a fiber optic cable;
   attaching a distal tip to said handle, said distal tip comprises a lens positioned adjacent to said illumination from said handle; and
   inserting a needle in an access port in a wall of said distal tip located a predetermined distance from the distal end of said distal tip for providing said therapeutic treatment to a lighted area at the end of said distal tip.

15. The method as recited in claim 14 further comprises the step of providing a light source to said fiber optic cable.

16. The method as recited in claim 14 further comprises the step of securing said distal tip to said handle with a set screw inserted into the handle to enable said distal tip to be easily removed after use.

* * * * *